United States Patent [19]
Elsasser, Jr.

[11] Patent Number: 5,646,306
[45] Date of Patent: Jul. 8, 1997

[54] PROCESS FOR CONTROLLED DEPOLYMERIZATION OF FEED MATERIAL TO PRODUCE A PRODUCT WITH LOWER MOLECULAR WEIGHT

[75] Inventor: A. Frederick Elsasser, Jr., Anderson Township, Hamilton County, Ohio

[73] Assignee: Henkel Corporation, Plymouth Meeting, Pa.

[21] Appl. No.: 624,338

[22] Filed: Apr. 3, 1996

Related U.S. Application Data

[63] Continuation of Ser. No. 315,663, Sep. 30, 1994, abandoned, which is a continuation of Ser. No. 667,135, Mar. 11, 1991, abandoned.

[51] Int. Cl.$^6$ ............... C07D 321/04; C07D 321/12
[52] U.S. Cl. ............................................. 549/267
[58] Field of Search ................................ 549/267

[56] References Cited

U.S. PATENT DOCUMENTS

| | | | |
|---|---|---|---|
| 4,650,851 | 3/1987 | Rhumi et al. | 549/274 |
| 4,709,058 | 11/1987 | Cahill et al. | 549/267 |
| 4,990,222 | 2/1991 | Aigner et al. | 549/274 |
| 5,043,458 | 8/1991 | Bhatia | 549/274 |

OTHER PUBLICATIONS

*Encyclopedia of Polymer Science and Engineering*, vol. 4, pp. 719–745 (John Wiley & Sons, New York, 1986), Mark et al. (editors).

*Primary Examiner*—Ba K. Trinh
*Attorney, Agent, or Firm*—John E. Drach; Norvell E. Wisdom, Jr.; Henry E. Millson, Jr.

[57] ABSTRACT

The practicality of known depolymerization reactions in which there is a danger of building up adherent residues on heat transfer surfaces is greatly improved by performing the process under conditions that provide a driving force which assures that none of the feed material and none of any liquid or solid residue produced during the depolymerization of the feed material remains in contact with any heat transfer surface for a time sufficiently long to form any adherent solid residue on the surface. A preferred apparatus for achieving such a driving force includes a horizontal thin film evaporator, a controlled continuous input of liquid feed material, and continuous collection of desired reaction product and any residue that remains condensed throughout its passage through the reaction zone. The process is especially well adapted to producing cyclic ethylene tridecanedioate, cyclic ethylene dodecanedioate, and cyclopentadecanolide from higher molecular weight feed materials such as linear polymers of these materials, in greater than 90% yield in a single pass.

20 Claims, 1 Drawing Sheet

PROCESS FOR CONTROLLED DEPOLYMERIZATION OF FEED MATERIAL TO PRODUCE A PRODUCT WITH LOWER MOLECULAR WEIGHT

This application is a continuation of application Ser. No. 08/315,663 filed on Sep. 30, 1994 now abandoned; which is a continuation of application Ser. No. 07/667,135 filed on Mar. 11, 1991 now abandoned.

BACKGROUND OF THE INVENTION

1. Field of the Invention

This invention relates to depolymerization processes which produce a product with lower molecular weight than the feed material. More particularly, this invention relates to the synthesis of cyclic esters from linear, branched, or higher molecular weight cyclic polyesters, especially those polyesters derivable from reaction of dicarboxylic acids with diols or from polymerization of monohydroxy monocarboxylic acids. Still more particularly, this invention is related to a process for synthesizing cyclic ethylene brassylate (also called "ethylene tridecanedioate"), cyclic ethylene dodecanedioate, and cyclopentadecanolide (also called "omega-pentadecalactone"), which are especially useful in perfumery.

2. Statement of Related Art

The general process of depolymerization is described by Mark et al. (editors), *Encyclopedia of Polymer Science and Engineering*, Volume 4, pages 719–745 (John Wiley & Sons, New York, 1986). A brief paragraph, with several literature citations, about the synthesis of cyclic compounds by depolymerization appears in this reference at the bottom of page 740.

This invention is particularly concerned with processes in which the product or products initially formed by depolymerization undergo further chemical reaction to produce the eventual desired product, especially a cyclic ester or lactone.

U.S. Pat. No. 4,709,058 of Nov. 24, 1987 to Cahill, Jr. et al. teaches the general primary art on which one specific embodiment of this invention is intended to improve. The entire specification of U.S. Pat. No. 4,709,058, except for any part that may be inconsistent with any explicit statement herein, is hereby incorporated herein by reference. The earlier prior art is reviewed in this Cahill patent.

In general terms, the Cahill patent teaches that the known reactions by which linear polyesters can be converted to cyclic compounds having from 8 to twenty carbon atoms in the cyclic ring are greatly improved for practical purposes when carried out in the presence of a polyolefin which is liquid but does not boil at the reaction temperature and which is chemically inert to the linear polyester feed material and the cyclic product at the temperature of the reaction.

The major teachings of Cahill are directed toward the benefits obtained by the presence of polyolefin during the reaction, and there is relatively little taught about mechanical reaction conditions. Cahill does teach the possibility of either batch or continuous reaction in general terms and gives at least one example of each, but in all cases the reactors taught by Cahill are stirred batch reactors.

In attempting to extend the processes taught by Cahill to longer reaction times than are explicitly taught therein, it has been found that a substantial amount of residue eventually accumulated in the reactor, and that during prolonged operation, the down time required for cleaning the reactor was at least half as great as the amount of useful operating time that could be achieved. A major object of this invention was to greatly increase the ratio of working time to time required for reactor cleaning in protracted operation of a process for producing cyclic compounds by decomposition of higher molecular weight polyesters.

DESCRIPTION OF THE INVENTION

In the following description, except in the claims and in the working and comparative examples or where explicitly stated to the contrary, all numbers specifying amounts of materials or conditions of reaction or use are to be understood as modified by the term "about" in defining the broadest scope of the invention. Practice within the exact numerical limits given is generally preferred, however.

SUMMARY OF THE INVENTION

It is believed that in stirred batch reactors of the type taught by Cahill, the average residence time of the feed and initial products of reaction can be controlled, but that at least in a thin zone near the walls of the reactor, and often in other "pockets" that may be present in the reactors taught by Cahill, there is no specific reliable driving force to control the maximum possible residence time. Practically useful conditions of reactor heating and average residence times in such reactors are believed to lead to the conversion of a portion of the feed material into exceptionally high viscosity products, which are less effectively moved by the stirring forces present in the reactor. Furthermore, the highest temperatures in such reactors are generally at the walls, where the stirring is least effective. It is therefore readily possible for part of the product to accumulate on or very near to the wall, where it remains for a much longer time than the average residence time of the feed material within the reactor. During sufficiently long residence time, such material eventually becomes solid residue which must be removed if the reactor is to continue to function in a practically useful manner, because the residue impedes the desired heat transfer from the heated reactor walls to the input feed material.

It has been found that the formation of undesired high molecular weight residues during depolymerization reactions can be avoided, without sacrificing other desirable characteristics of prior art processes, by using apparatus in which the residence time of feed material and/or solid residue is controllable by a positive driving force. The most generally convenient and cheaply available positive driving force is that of gravity, which is used in most embodiments of this invention. However, other driving forces such as flexible blade intermittent scrapers and the like are readily conceivable to those skilled in the art and are within the scope of this invention.

DESCRIPTION OF PREFERRED EMBODIMENTS

Figure 1:
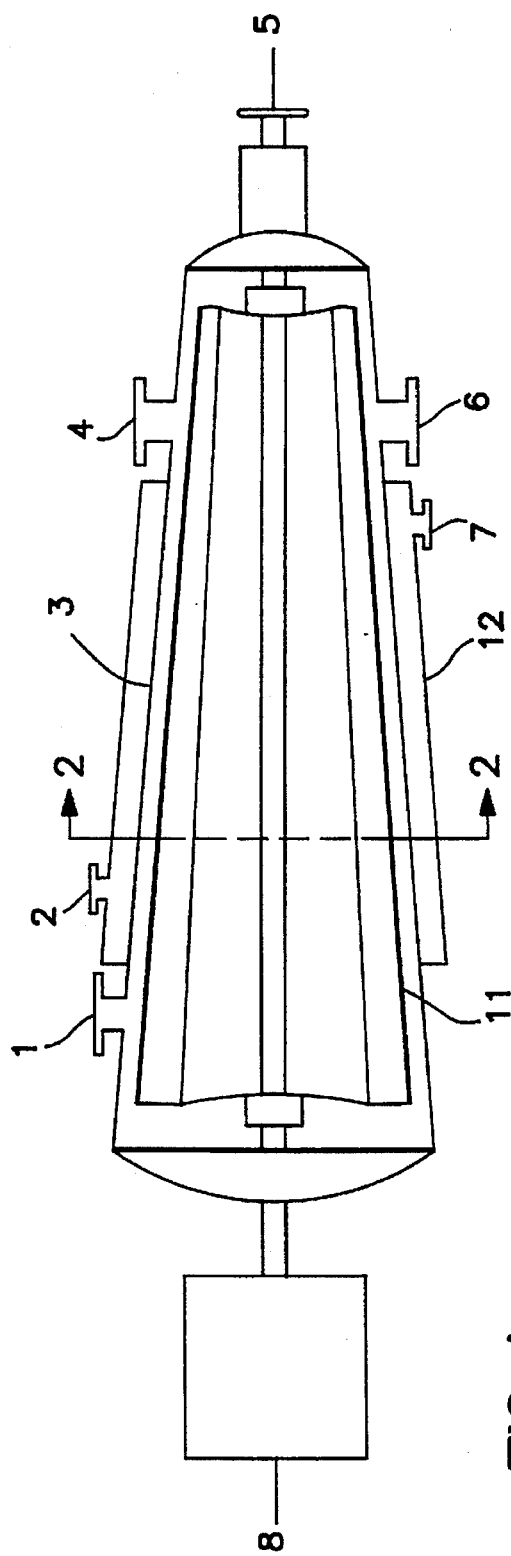
FIG. 1 is a side elevation view, partially broken away, of a preferred apparatus, of the type known as a "horizontal thin film evaporator", for performing a process according to this invention.

One important class of embodiments of the present invention includes processes in which at least the solid and liquid phase materials among the reagent(s), reaction product(s), decomposition catalyst(s), and polyolefin(s) when used are confined, while at reaction temperature, within a reaction zone having a thickness no greater than 20 millimeters ("mm") or with increasing preference, no greater than 3.0, 2.3, 1.9, or 1.5 mm. The thickness of the reaction zone, irrespective of the exact shape of the zone, is defined as the smallest number "t" having the property that, from any selected point within the reaction zone, an imaginary sphere with its center at the selected point and with a diameter greater than "t" mm will include some space not within the reaction zone. The reaction zone should be surrounded by a gas tight enclosure, so that the gas pressure within and around the reaction zone can be controlled.

The reaction temperature should be high enough for the vapor pressure of the desired product to be at least 1, or increasingly preferably at least 4.7, 9.6, 19, or 31 times the pressure maintained around the reaction zone. This temperature is denoted herein as the "volatility limit temperature" or "lower limit temperature." On the other hand, the reaction temperature should be low enough to permit decomposition of the desired product at no more than 10, or with increasing preference, no more than 5, 2.2, or 1, % per hour. This temperature is denoted herein as the "decomposition limit temperature" or "upper limit temperature." For most products of current practical interest, the pressure around the reaction zone must be maintained fairly low, e.g., not more than 10 torrs, in order to leave any available reaction temperature between the upper and lower limits as defined above. Otherwise, however, the reaction(s) appear relatively insensitive to pressure.

The solid and/or liquid materials introduced into the reaction zone as described above should remain there long enough to cause at least some of the desired depolymerization product to be formed, either directly by decomposition of the introduced higher molecular weight feed material or by reaction of intermediate chemical species produced during depolymerization, and for the desired product to pass as vapor out of the reaction zone and into a condensation zone, which is distinct from the reaction zone, but still within the gas tight enclosure that also encloses the reaction zone. The condensation zone contains a condenser, where the vapor will condense and can be collected separately from any residual solid and liquid remaining in the reaction zone.

It is highly preferred that the reaction(s) to produce the desired compound(s) desired be performed in a continuous manner. For example, in the especially preferred embodiments in which the major reaction product is cyclic ethylene brassylate, cyclic ethylene dodecanedioate, or cyclopentadecanolide, (i) a solid and/or liquid feed material containing at least depolymerization catalyst and reactant feed material containing linear or higher cyclic polymers that will produce the desired product upon decomposition, and, optionally but preferably, polyolefin, is fed into one end of the reactor volume and a flow is induced from the point of introduction into the reactor volume to the other end of the reaction zone, (ii) the part of the feed mixture which remains solid or liquid during its residence time within the reaction zone flows through the entire reaction zone, becoming mixed during this flow with any solid or liquid reaction products and being removed from the reaction zone as residue at the end of the reaction zone opposite that at which the feed enters, and (iii) the desired cyclic product or products pass continually from the reaction zone into a gas phase that is connected to the condensation zone and are recovered for use by condensation from this gaseous phase.

In a continuous process embodiment of the invention such as is described immediately above, the feed rate of reaction mixture to the reaction zone has been found to be one of the variables with the greatest effect on the practical value of the results achieved by the process. It is believed that the effect of the feed rate on the results is a consequence of the correlated variation of residence time in the reaction zone. This residence time is determined by at least four characteristics of the process: the feed rate in mass per unit time, the density of the mixture of feed materials and reaction products within the reaction zone; the volume of the reaction zone, and the rate at and extent to which a portion of the input feed material may be volatilized from the reaction zone during passage therethrough, thereby making more of the reaction zone available for receiving additional solid and/or liquid feed material and increasing the actual residence time for the part of the feed that remains condensed during its passage through the reaction zone.

The "nominal residence time" is defined for purposes of this description as the quotient of the volume of the reaction zone divided by the feed rate in volume per unit time. This would be the actual residence time if (i) there were no volatilization from the reaction zone and (ii) the feed material had the same density in the reaction zone as it did at the temperature of measuring the volume input rate of the feed to the reaction zone. In practice, the density is expected to be at least slightly less in the reaction zone than at the point where volume input rates are measured, because the reaction zone is hotter, and the fraction of volatilization is considerable. The net result is that the actual residence times are believed normally to be from about three to about seven times the calculated nominal residence times.

Under normal operating conditions in a continuous process, the reaction zone volume does not change during the process, but the density in the reaction zone and the exact kinetics and extent of volatilization are difficult to predict theoretically and sometimes are difficult to influence in any simple manner in practice. The major means of practical control of a continuous embodiment are control of the size of the reaction zone, the feed rate, the feed composition, the temperature(s) within the reaction zone, and the mechanical conditions favoring or limiting the transfer rate of reaction product gases away from contact with, and thus from effective participation in chemical equilibria with, the solid and liquid contents of the reaction zone. Among these mechanical conditions, the most important ones normally are the pressure of the gas in contact with the reaction zone, the nature and extent of mechanical motion(s) promoting mixing and/or transport in a favored direction of the gas in contact with the reaction zone, the gas permeability or lack thereof in the surfaces which define the major boundaries of the reaction zone, and the temperature difference between the reaction zone and the condenser(s) used for collection of the cyclic products.

The suitable and preferred relative amounts of linear polyester, catalyst, and polyolefin to make up a feed mixture for use according to this invention are generally the same as are set forth in the above mentioned U.S. Pat. No. 4,709,058, except that it has been found that the ratio of polyolefin to polyester preferably is much lower for a process according to this invention. Specifically, the ratio by weight of polyolefin to polyester for a feed mixture for a process according to this invention is preferably from 0.1 to 0.003, or more preferably from 0.01 to 0.03. Operation without any polyolefin is possible but usually less preferred, because the maximum conversion per pass that can be achieved without forming adherent solid residue on any part of the reactor is less.

Perhaps the simplest apparatus useful for a process according to this invention includes a heated tilted plane contact surface maintained within a vacuum tight space and supplied along its upper edge with molten feed material. The feed material is positively driven toward the lower edge of the heated tilted surface by the force of gravity, at a rate which is controlled by the angle of tilt and the viscosity of the mixture of the part of the feed that remains condensed and of any condensed phase reaction products that are formed from it. Gaseous depolymerization products and/or products of further reaction of such gaseous depolymerization products are recovered by condensation on a colder surface maintained within the vacuum tight space surrounding the heated tilted surface. For general depolymerization reactions according to this invention, conventional falling film reactors may also be useful, but for the specific chemical embodiment of greatest interest, the synthesis of macrocyclic esters useful in perfumery, the residence time in such conventional falling film reactors is generally too short to be preferred.

The currently most preferred equipment for practical performance of a process according to this invention for producing macrocyclic esters includes a commercially available item of equipment known as a "horizontal thin film evaporator", which has generally been used in the past, as its name implies, predominantly for physical separation processes.

Figure 2:
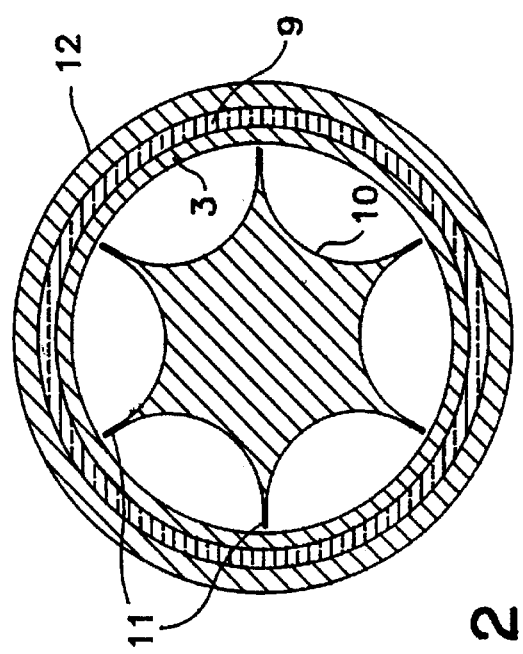
FIG. 2 is cross-sectional view from the left side of FIG. 1, along the line A—A in FIG. 1, but at a larger scale than in FIG. 1.

The mechanical parts of such equipment which are particularly important to its use in this invention are illustrated in the drawing figures. A metal shell 3 in the shape of a conic frustrum as shown defines a gas tight enclosure having inlet 1 and outlets 4 and 6. A portion of this shell 3 also defines the outer boundary of the reaction zone used in the invention. Much of the interior of the equipment is filled with a rotor 10 with the cross-section shape shown in FIG. 2, with six blade holders holding blades 11 at the extreme periphery of the rotor. The position of the rotor with respect to the shell 3 can be adjusted through conventional mechanical means not shown in detail via adjustment control 5. As the rotor 3 is moved to the right in FIG. 1, the gap between the blades 11 and the shell 3 narrows; if the rotor is moved to the left instead, the gap widens.

During use, the rotor, driven by motor 8, moves at about 400–600 revolutions per minute ("rpm"). This speed is sufficient to confine substantially all the condensed phase (i.e., liquid or solid) material within the reactor in a thin zone between the shell 3 and the imaginary surface of rotation defined by the edges of the rotating blades 11. Gaseous products of reaction, on the other hand, can pass readily through the spaces between the blades to exit port 4, through which they are withdrawn into the condensation zone of the invention, which is conventional and not shown in the drawings.

The rotation axis of these surfaces of rotation that serve as the major boundaries of the reaction zone is approximately horizontal, and, as noted above, the inner imaginary surface of rotation bounding the reaction zone is rotated during use by rotating the blades that define it. If the rate of introduction of feed material into such a reaction zone is slow, the residence time can be increased within very broad limits. The gravitational force existing by reason of the difference in height between feed inlet port 1 and residue exit port 6 is sufficient to assure that none of the input feed or liquid or solid residue produced from the feed remains in the reactor for an uncontrolled length of time, but the difference in height between the inlet and outlet ports is sufficiently small, and the gravitationally induced net direction of flow is superimposed on a sufficiently large rotational motion within the reactor, that the average residence time can be controlled to be as high as at least tens of minutes. As shown below, this time is sufficient to produce a very high conversion of input feed to the macrocyclic ester products desired in one embodiment of this invention. In contrast, in a more common vertical or falling film reactor, which often is much like the horizontal thin film evaporator, except that the axes of the surfaces of rotation that define the reaction zone are vertical, the larger difference in height between the inlet and outlet ports limits the maximum residence time that can be practically achieved to a value too low for high conversions under the reaction conditions now preferred for making macrocyclic esters according to this invention.

The practice of the invention may be further appreciated from the following specific working examples, which are not to be understood as limiting the invention. The examples are generally set forth for synthesis of cyclic ethylene brassylate, but are equally applicable to the synthesis of cyclic ethylene dodecanedioate or other cyclic compounds with similar volatility characteristics, such as cyclopentadecanolide.

EXAMPLES

In these examples, the reaction zone for the process according to this invention was provided by a SAKO™ Model KH 40 Horizontal Thin Film Evaporator (hereinafter "HTFE"), commercially available from Luwa Corp., Charlotte, N.C., 28297-6348, USA or from Buss AG, CH-4133 Pratteln 1, Switzerland. The outer major boundary of the reaction zone provided by this apparatus is a metal shell (item 3 in the drawings) in the shape of a conic frustrum about 0.9 meters long and about 0.2 meters in diameter at its midpoint, providing a total surface area of about 0.4 square meters ("$m^2$") between its inlet and outlet ports. The axis of this conic frustrum surface defining the outer boundary of the reaction zone is substantially horizontal. A set of six metal blades mounted on a rotatable metal frame as generally illustrated in the drawing figures herein provides the inner boundary of the reaction zone by rotation during use. The axis of rotation of the blades is substantially coincident with the axis of the outer boundary surface. The thickness of the reaction zone is determined by the extent of linear displacement along their common axes between the outer boundary surface and the outer tips of the blades. This thickness can be varied continuously between about 20 and about 0.7 mm.

During operation of the HTFE, feed material that has been preheated sufficiently to flow easily and to raise its temperature to nearly but not quite the temperature desired for the reaction is fed by a conventional metering pump (not shown in the drawings) through inlet port 1 into the reaction zone near the larger end of metal shell 3 of the HTFE. Shell 3 is heated by a conventional circulating hot oil heating system, which pumps hot oil 9 through oil inlet port 7 into a heating fluid space between shell 3 and heating fluid space outer jacket 12; the oil exits through oil outlet port 2 and is conventionally recirculated to the heating system. By contact with heated shell 3, the reaction mixture is heated to the reaction temperature. The reaction mixture and products, including gaseous products, flow toward the smaller end of the conical reaction zone as well as around the axis of the zone. That part of the reaction mixture and products which remains liquid or solid during passage through the reaction zone flows downward through exit port 6 into a conventional collection system not shown.

Gaseous products of reaction flow upward from this small end of the reaction zone, through a large diameter pipe (about 300 mm in diameter), provided with conventional heating means to prevent blockage by solidified product, to a conventional conical entrainment separator and from there in succession to a conventional primary condenser cooled with tempered glycol heat transfer fluid and a conventional secondary condenser cooled with chilled glycol heat transfer fluid. Both primary and secondary condensers were of the shell-and-tube type, with about 3 $m^2$ each of condensing surface. Glycol based heat transfer fluid, at an inlet temperature of about 50° C. for the primary condenser and about 4° C. for the secondary condenser, was continuously circulated through the condensers during operation of the process. Vacuum inducing means, such as mechanical pump(s) or steam ejector(s), were connected to the gas space that includes the volume between the reaction zone and rotor 10, with the condensers situated between the vacuum inducing means and the reaction zone. The condensate from each condenser and the non-gaseous phases from the entrainment separator can all be collected separately.

For the first group of examples, the feed mixture composition was 96 percent by weight (hereinafter "w/o") of polyethylene brassylate prepared as described in the above mentioned U.S. Pat. No. 4,709,058 between column 6 line 53 and column 7 line 10; 2 w/o of homopolymer polyethylene wax having a Mettler Drop Point measured according to ASTM D-3104 of 102° C., a hardness of 7.0 dmm measured according to ASTM D-5, a specific gravity of 0.91 as measured according to ASTM D-1505, a viscosity of 180 centipoises at 140° C. measured with a Brookfield viscosimeter, and a vapor pressure of no more than 6 torrs at 340° C. (commercially available as A-C™ 617 from Allied Corp., Morristown, N.J.); and 2 w/o of a mixed potassium aluminum salt having the formula shown in column 7 lines 11–12 of U.S. Pat. No. 4,709,058. For the second group of examples, the components of the feed mixture were the same as above, but the amount of polyethylene and of the potassium aluminum salt catalyst were reduced slightly below those specified above. For the third group, the feed material was a mixture of the same type of material as for the first group with material (hereinafter denoted as "residue" or "residue material") that had been collected as solid and/or liquid at the end of the reaction zone during processing of feed of the type indicated for the first or second group; the exact proportions of mixing were not determined. For the fourth group of examples, the feed was entirely composed of residue material. Some important characteristics of the examples are shown in Table 1.

TABLE 1

DATA ON PRODUCTION OF CYCLIC ETHYLENE BRASSYLATE

| Example No. | Pressure, Torrs | Product Boiling Point, °C. | Reaction Zone Temperature, °C. | Feed Rate, Kg/hr | Reaction Zone Thickness, mm. | Rotor Speed, RPM | Nominal Residence Time, Min. | Weight Percent of Feed Recovered as Distillate |
|---|---|---|---|---|---|---|---|---|
| | | | | First Group | | | | |
| 1 | 3.5 | 179 | 338 | 55 | 1.4 | 500 | 0.6 | 12 |
| 2 | 3.0 | 173 | 337 | 23 | 1.2 | 500 | 1.2 | 66 |
| 3 | 3.5 | 179 | 339 | 34 | 1.2 | 500 | 0.8 | 31 |
| 4 | 4.5 | 188 | 349 | 36 | 1.2 | 500 | 0.8 | 29 |
| 5 | 6.0 | 199 | 349 | 39 | 1.2 | 498 | 0.7 | 28 |
| | | | | Second Group | | | | |
| 6 | 0.8 | 131 | 312 | 15 | 1.2 | 495 | 1.9 | 45 |
| 7 | 0.8 | 131 | 312 | 28 | 1.5 | 502 | 1.3 | 9 |
| 8 | 0.9 | 134 | 322 | 31 | 1.5 | 502 | 1.2 | 14 |
| 9 | 1.0 | 137 | 332 | 7.6 | 1.5 | 502 | 4.7 | 98 |
| 10 | 1.5 | 150 | 321 | 5.5 | 1.5 | 502 | 6.5 | 98 |
| 11 | 1.5 | 150 | 321 | 5.7 | 1.5 | 502 | 6.3 | 99 |
| | | | | Third Group | | | | |
| 12 | 5.5 | 196 | 349 | 27 | 1.2 | 501 | 1.1 | 15 |
| 13 | 5.5 | 196 | 349 | 24 | 1.1 | 500 | 1.1 | 17 |
| 14 | 6.0 | 199 | 348 | 25 | 1.4 | 501 | 1.3 | 11 |
| 15 | 6.0 | 199 | 348 | 18 | 0.9 | 500 | 1.2 | 23 |
| 16 | 6.5 | 203 | 348 | 29 | 0.8 | 500 | 0.7 | 8 |
| 17 | 6.5 | 203 | 348 | 29 | 0.9 | 600 | 0.7 | 10 |
| 18 | 5.0 | 192 | 348 | 30 | 0.9 | 400 | 0.7 | 8 |
| | | | | Fourth Group | | | | |
| 19 | 0.8 | 131 | 312 | 19 | 1.2 | 502 | 1.5 | 11 |

Notes for Table 1

The boiling point listed in the third column of the table is for the pressure listed in the second column. The "Nominal Residence Times" shown were calculated by dividing the nominal reaction zone volume in cubic centimeters (=4000{reaction zone thickness in centimeters}) by the feed rate in kilograms per minute. This would be the same as the "nominal residence time" defined in the text if the density of the feed mixture were exactly 1 gram per cubic centimeter; it is believed that the actual density of the feed material approximates this value. Other values listed were measured directly or calculated by well established equations from measured values.

During the performance of the examples shown in Table 1, it was observed that when the reaction temperature was higher than 340° C., there was a substantial danger of obstructing the gas exit space with solid and/or liquid materials. It is believed that these obstructing materials resulted from the decomposition of the desired product cyclic ethylene brassylate and/or of the polyethylene used in the reaction feed. Operation of the reaction at not more than 340° C. is therefore preferred, and at such temperatures, no significant accumulation of immobile solids within the reaction zone was observed. The temperature range for this reaction more preferably is 320–335, or still more preferably 330–335, °C.

The data for the first and second groups in Table 1, and some similar data not shown because they were under less preferred conditions of operation, indicate that the most important variable controlling the degree of conversion to the desired cyclic product is residence time. Excluding Examples 6 and 7, for which the reaction temperature was lower than optimum, all the remaining examples in the first and second groups show a generally linear correlation, although with substantial fluctuations, between percent conversion and nominal residence time for nominal residence times between about 0.6 and 5 minutes.

The feed rate, as noted above, is more reliably measurable than the actual residence time, and the percent conversion was found to be approximately linearly correlated with the reciprocal of the feed rate to the power 2.4. Higher temperature favors conversion slightly, but there is little difference for temperatures over about 320° C. Pressures and reaction zone thickness within the ranges listed in Table 1 have only a slight effect if any on the percent conversion of feed to the desired product. The smaller amounts of catalyst and polyethylene in the feed for the second group have a slightly negative effect on the percent conversion, compared with the first group, but very high conversions are still possible at sufficiently low feed rates, as shown by Examples 9–11.

Comparison of the third and fourth groups with the first and second groups shows that the percent conversion is markedly smaller for feed material that is residue from a former pass through the reaction zone, compared with "virgin" poly{ethylene brassylate} feed. Residue material can be converted to the desired product, but in view of the high yields obtainable from slow single passes through an appropriate reaction zone as illustrated by Examples 9–11, it appears economically preferable to use only "virgin" poly{ethylene brassylate} in the feed, operate at conditions to give a conversion of at least 90% of the input poly{ethylene brassylate} to cyclic ethylene brassylate in a single pass, and discard the small fraction of residue thereby produced.

Cyclic materials produced according to this invention, like those described in the above referenced U.S. Pat. No. 4,709,058, are high in quality and free from any significant amounts of contaminants that would restrict the desired use of the cyclic products in perfumery and cosmetics, either by discoloration or by adverse effects on odor.

What is claimed is:

1. In a depolymerization process for the synthesis of cyclic esters from linear polyesters, branched polyesters, or higher molecular weight cyclic polyesters wherein a liquid or solid polyester feed material is contacted with a heated, solid, chemically inert surface, the improvement wherein the process comprises the steps of:

(A) contacting said liquid or solid feed material with a heated, solid, chemically inert surface in a reaction zone having a thickness not greater than 20 mm for a contact time sufficient to cause at least part of the feed material to depolymerize and react to form a gaseous cyclic ester product, in the presence of a positive driving force which assures that none of the feed material and none of any liquid or solid residue coproduced therefrom during the depolymerization of the feed material remains in contact with said heated, solid, chemically inert surface for a time sufficiently long to form a solid residue that adheres to said heated, solid, chemically inert surface, and wherein said heated, solid, chemically inert surface is a part of the boundary of said reaction zone, said reaction zone being surrounded by a gas tight enclosure and being connected via a passageway freely traversable by vapor to a condensation zone distinct from but within the same gas tight enclosure as is the reaction zone; and (B) passing the gaseous cyclic ester product from step (A) to said condensation zone to condense the gaseous cyclic ester product therein.

2. A process according to claim 1 wherein in step (A) a direction of net flow of mass through the reaction zone is established and feed material is continuously introduced at a controlled rate into the reaction zone at the input end of this direction of net flow of mass and product in vapor phase is continuously removed from the output end of the direction of net flow of mass through the reaction zone.

3. A process according to claim 1, wherein said cyclic ester reaction product includes material selected from the group consisting of cyclic ethylene brassylate, cyclic ethylene dodecanedioate, and cyclopentadecanolide.

4. A process according to claim 3, wherein the nominal residence time in the reaction zone is at least 1 minute.

5. A process according to claim 4, wherein the thickness of the reaction zone is not greater than about 1.5 mm, the pressure in the condensation zone and the pressure surrounding the reaction zone are not greater than about 3 torrs, and the temperature in the reaction zone is in the range from about 320–about 335 degrees C.

6. A process according to claim 5, wherein the pressure in the condensation zone and the pressure surrounding the reaction zone are not greater than about 1.5 torrs and the temperature in the reaction zone is in the range from about 330–about 335 degrees C.

7. A process according to claim 6, wherein said reaction product includes a total mass of material selected from the group consisting of cyclic ethylene brassylate, cyclic ethylene dodecanedioate, and cyclopentadecanolide that is equal to at least 90 percent of the mass of feed material introduced into the process.

8. A process according to claim 5, wherein said reaction product includes a total mass of material selected from the group consisting of cyclic ethylene brassylate, cyclic ethylene dodecanedioate, and cyclopentadecanolide that is equal to at least 90 percent of the mass of feed material introduced into the process.

9. A process according to claim 4, wherein said reaction product includes a total mass of material selected from the group consisting of cyclic ethylene brassylate, cyclic ethylene dodecanedioate, and cyclopentadecanolide that is equal to at least 90 percent of the mass of feed material introduced into the process.

10. A process according to claim 3, wherein said reaction product includes a total mass of material selected from the group consisting of cyclic ethylene brassylate, cyclic ethylene dodecanedioate, and cyclopentadecanolide that is equal to at least 90 percent of the mass of feed material introduced into the process.

11. A process according to claim 10 wherein the reaction zone is bounded by concentric inner and outer boundary surfaces of rotation in a horizontal thin film evaporator and one of the boundary surfaces is rotated during the process at a rate of at least about 400 revolutions per minute to provide mixing within the reaction zone.

12. A process according to claim 9 wherein the reaction zone is bounded by concentric inner and outer boundary surfaces of rotation in a horizontal thin film evaporator and one of the boundary surfaces is rotated during the process at a rate of at least about 400 revolutions per minute to provide mixing within the reaction zone.

13. A process according to claim 8 wherein the reaction zone is bounded by concentric inner and outer boundary surfaces of rotation in a horizontal thin film evaporator and one of the boundary surfaces is rotated during the process at a rate of at least about 400 revolutions per minute to provide mixing within the reaction zone.

14. A process according to claim 5 wherein the reaction zone is bounded by concentric inner and outer boundary surfaces of rotation in a horizontal thin film evaporator and one of the boundary surfaces is rotated during the process at a rate of at least about 400 revolutions per minute to provide mixing within the reaction zone.

15. A process according to claim 4 wherein the reaction zone is bounded by concentric inner and outer boundary surfaces of rotation in a horizontal thin film evaporator and one of the boundary surfaces is rotated during the process at a rate of at least about 400 revolutions per minute to provide mixing within the reaction zone.

16. A process according to claim 3 wherein the reaction zone is bounded by concentric inner and outer boundary surfaces of rotation in a horizontal thin film evaporator and one of the boundary surfaces is rotated during the process at a rate of at least about 400 revolutions per minute to provide mixing within the reaction zone.

17. In a depolymerization process wherein a liquid or solid feed material containing a polymeric compound is contacted with a heated, solid, chemically inert surface, the improvement wherein the process comprises the steps of:

(A) contacting said liquid or solid feed material with a heated, solid, chemically inert surface in a reaction zone having a thickness not greater than 20 mm for a contact time sufficient to cause at least part of the feed material to depolymerize to a gaseous product of lower molecular weight than the feed material, which gaseous product may undergo further chemical reaction to form another desired gaseous product, in the presence of a positive driving force which assures that none of the feed material and none of any liquid or solid residue coproduced therefrom during the depolymerization of the feed material remains in contact with said heated, solid, chemically inert surface for a time sufficiently long to form a solid residue that adheres to said heated, solid, chemically inert surface, and wherein said heated, solid, chemically inert surface is a part of the boundary of said reaction zone, said reaction zone being surrounded by a gas tight enclosure and being connected via a passageway freely traversable by vapor to a condensation zone distinct from but within the same gas tight enclosure as is the reaction zone; and (B) passing the gaseous product from step (A) to said condensation zone to condense the gaseous product therein.

18. The process of claim 17 wherein in step (A) the reaction zone has a thickness not greater than about 3.0 mm.

19. A process according to claim 17 wherein in step (A) a direction of net flow of mass through the reaction zone is established and feed material is continuously introduced at a controlled rate into the reaction zone at the input end of this direction of net flow of mass and product in vapor phase is continuously removed from the output end of the direction of net flow of mass through the reaction zone.

20. A process according to claim 17 wherein the reaction zone is bounded by concentric inner and outer boundary surfaces of rotation in a horizontal thin film evaporator and one of the boundary surfaces is rotated during the process at a rate of at least about 400 revolutions per minute to provide mixing within the reaction zone.

* * * * *